US012773492B2

(12) United States Patent
Fischer

(10) Patent No.: US 12,773,492 B2
(45) Date of Patent: Oct. 27, 2026

(54) SUSPENSION TETHER FOR MEDICAL TUBING AND ATTACHMENT DEVICE FOR SAME

(71) Applicant: Morgan Fischer, Upper Brookville, NY (US)

(72) Inventor: Morgan Fischer, Upper Brookville, NY (US)

( * ) Notice: Subject to any disclaimer, the term of this patent is extended or adjusted under 35 U.S.C. 154(b) by 489 days.

(21) Appl. No.: 16/477,385

(22) PCT Filed: Jan. 11, 2018

(86) PCT No.: PCT/US2018/013337
§ 371 (c)(1),
(2) Date: Jul. 11, 2019

(87) PCT Pub. No.: WO2018/132584
PCT Pub. Date: Jul. 19, 2018

(65) Prior Publication Data

US 2020/0023120 A1 Jan. 23, 2020

Related U.S. Application Data

(60) Provisional application No. 62/445,125, filed on Jan. 11, 2017.

(51) Int. Cl.
*A61M 5/14* (2006.01)
*A61M 25/02* (2006.01)

(52) U.S. Cl.
CPC ........ *A61M 5/1418* (2013.01); *A61M 5/1415* (2013.01); *A61M 25/02* (2013.01);
(Continued)

(58) Field of Classification Search
CPC ................ A61M 25/02; A61M 5/1418; A61M 2025/028; A61M 39/00;
(Continued)

(56) References Cited

U.S. PATENT DOCUMENTS 2,506,783 A * 5/1950 Fauteux, Jr. ........... D06F 55/00 24/532
2,882,071 A 4/1959 Klompar
(Continued)

OTHER PUBLICATIONS

"Strap." Cambridge Dictionary, 2022. Cambridge University Press. Accessed Aug. 24, 2022 <https://dictionary.cambridge.org/us/dictionary/english/strap> (Year: 2022).*
(Continued)

*Primary Examiner* — Scott J Medway
(74) *Attorney, Agent, or Firm* — Carter, DeLuca & Farrell LLP

(57) ABSTRACT

A suspension tether suspends intravenous medical tubing that extends between a patient and an IV stand, which supports an IV solution source. The suspension tether includes an elongate elastic body member connectable at one end to a hook of the IV stand and connected at the other end to the IV tube(s). The suspension tether facilitates patient mobility by allowing the patient to move about a space relative to the IV stand to a distance near the full length of the IV tubing with lessened risk of pulling the tubing tight, disengaging the IV line, harming the patient, or damaging equipment. More importantly, the suspension tether suspends the IV tubing off the floor, away from the patient's feet and legs and the stand's wheels, so that the patient may roll the IV stand along his/her side while walking around without risk of entanglement of the IV tube or tripping on the IV tube.

53 Claims, 6 Drawing Sheets

(52) U.S. Cl.
CPC ................. *A61M 2025/024* (2013.01); *A61M 2025/0253* (2013.01)

(58) Field of Classification Search
CPC .... A61M 2205/0216; A61M 2209/082; A61M 2209/084; A61M 5/1415; A61M 5/1417; Y10S 128/26; A61G 13/101; F16B 2/005; F16B 45/00
See application file for complete search history.

(56) References Cited

U.S. PATENT DOCUMENTS 3,203,061 A * 8/1965 Thomas ............... A47G 25/485 24/338
3,521,332 A * 7/1970 Kramer ................. F16B 5/0685 403/188
3,834,380 A * 9/1974 Boyd .................... A61M 25/02 604/180
4,277,863 A * 7/1981 Faneuf .................. A44B 99/00 224/247
4,277,864 A * 7/1981 Orson, Sr. .............. A44B 99/00 24/327
4,308,642 A * 1/1982 Heyman ................ A44B 99/00 128/DIG. 26
4,402,669 A * 9/1983 Frazier ..................... A61C 7/06 433/5
4,639,980 A * 2/1987 Peterson ............... A61M 25/02 128/DIG. 14
4,666,111 A 5/1987 Schuler
4,690,674 A * 9/1987 Dalglish .............. A61G 7/0524 604/93.01
4,707,906 A 11/1987 Posey
4,711,636 A * 12/1987 Bierman ............... A61M 25/02 128/DIG. 26
4,745,883 A * 5/1988 Baggetta .............. A47D 13/086 119/770
4,896,465 A * 1/1990 Rhodes ............... A61M 5/1418 128/849
4,977,011 A * 12/1990 Smith ....................... B32B 5/04 428/152
D322,390 S * 12/1991 Nimtz ............................ D8/395
5,090,408 A * 2/1992 Spofford ........... A61M 16/0472 128/207.14
5,163,923 A * 11/1992 Donawick ........... A61M 5/1418 119/72
5,209,562 A * 5/1993 Glassford ............... F21S 6/003 362/294
5,226,892 A 7/1993 Boswell
5,242,407 A * 9/1993 Struble ................. A61M 5/142 417/474
5,279,486 A * 1/1994 Harmon ............... A61G 7/0503 248/122.1
5,334,186 A * 8/1994 Alexander .......... A61M 5/1418 128/DIG. 15
5,336,179 A * 8/1994 Ryan ................... A61M 5/1418 128/DIG. 26
5,361,726 A * 11/1994 Harris .................. A01K 27/005 119/797
5,370,246 A * 12/1994 Traynor ............... A61G 7/0503 5/503.1
5,615,454 A * 4/1997 Contarino ............. A45C 13/20 24/116 A
5,702,175 A * 12/1997 Chen ....................... F21V 21/08 362/184
5,735,822 A 4/1998 Steins
5,776,105 A * 7/1998 Corn ................... A61M 5/1483 604/179
5,785,011 A 7/1998 Gittermann, III
5,795,335 A 8/1998 Zinreich
5,830,180 A * 11/1998 Chandler ............ A61M 3/0258 604/65
5,871,189 A * 2/1999 Hoftman .............. A61G 7/0503 248/229.16
5,884,372 A * 3/1999 Anscher .................... F16L 3/02 24/3.12
6,158,095 A * 12/2000 Lassiter .................. F16L 3/237 24/129 R
6,247,211 B1 6/2001 Bell
6,669,712 B1 * 12/2003 Cardoso ............ A61M 16/0683 128/207.18
6,813,814 B1 * 11/2004 Schultz .................. A44B 99/00 24/545
7,201,739 B2 * 4/2007 Walborn ............... A61M 25/02 604/178
7,287,489 B1 * 10/2007 O'Brien ................ A01M 29/12 119/712
7,559,125 B2 * 7/2009 Cofer .................. A61M 5/1418 24/487
7,744,043 B2 6/2010 Otinger
7,805,849 B1 * 10/2010 Baker, Jr. ................. G01C 9/34 33/379
8,146,210 B2 * 4/2012 Nishtala .............. A61M 5/1418 24/16 R
D678,533 S * 3/2013 Bernstein ..................... D24/187
8,597,254 B1 * 12/2013 Mullet ................ A61M 5/1418 604/174
8,998,151 B2 * 4/2015 Hoek ....................... H02G 3/32 248/68.1
9,374,984 B2 * 6/2016 McCay ................ A01K 27/003
9,511,185 B2 * 12/2016 Slaker ................. A61M 5/1418
9,808,573 B1 * 11/2017 Dooley ............... A61M 5/1415
9,878,088 B2 * 1/2018 Mellard .............. A61M 5/1418
10,322,055 B1 * 6/2019 Davis ....................... A61H 3/04
10,493,243 B1 * 12/2019 Braham .................... F16B 2/10
10,499,899 B2 * 12/2019 Lee ......................... A61M 1/00
10,583,243 B2 * 3/2020 Burke ................... A61M 25/02
10,640,913 B2 * 5/2020 Bailey ...................... D06C 3/04
10,813,439 B2 * 10/2020 Huang ...................... F16B 2/10
10,835,667 B1 * 11/2020 Rogers ................ A61M 5/1417
10,881,782 B2 * 1/2021 Behrens ................ F16L 3/2235
2001/0049504 A1 * 12/2001 Gautsche ............... A61B 46/23 604/174
2002/0096608 A1 7/2002 Cedarberg
2002/0116802 A1 * 8/2002 Moerman ................. D01F 6/62 28/258
2006/0113432 A1 * 6/2006 Driskell .................... F16L 3/26 248/68.1
2006/0249635 A1 * 11/2006 Newkirk .............. A61G 7/0503 248/74.1
2006/0271019 A1 * 11/2006 Stoller .................. A61F 5/4404 604/353
2007/0106263 A1 * 5/2007 Ward ...................... A61M 5/14 604/533
2007/0123841 A1 5/2007 Egan
2007/0142785 A1 6/2007 Lundgaard et al.
2007/0215759 A1 * 9/2007 Heegaard ............ A61M 5/1418 248/90
2007/0259555 A1 11/2007 Conforti
2010/0298813 A1 11/2010 Kudo
2010/0326371 A1 * 12/2010 Lopusnak ............ A01K 27/004 119/796
2011/0023208 A1 * 2/2011 Liao ...................... A61M 25/02 2/102
2013/0046242 A1 2/2013 Harris
2013/0310771 A1 * 11/2013 Karlin ................... A61M 39/08 604/263
2014/0213980 A1 * 7/2014 Filippelli ............. A61M 25/02 604/179
2014/0306070 A1 * 10/2014 Hartsock ............. A61M 5/1418 248/68.1
2015/0297826 A1 * 10/2015 Slaker ................. A61M 5/1418 248/560
2016/0256360 A1 * 9/2016 Goodwin ............ A61M 5/1418
2016/0296726 A1 * 10/2016 Navarro Mallach . A61M 25/02
2018/0064502 A1 * 3/2018 Shamir ..................... F16B 2/22
2018/0200485 A1 * 7/2018 Braham ............ A61M 16/0051

(56) References Cited

U.S. PATENT DOCUMENTS

| | | | | |
|---|---|---|---|---|
| 2019/0003087 | A1* | 1/2019 | Matsumoto | D04B 1/246 |
| 2019/0282793 | A1* | 9/2019 | Stafford | A61M 39/08 |

OTHER PUBLICATIONS

International Search Report and Written Opinion issued Apr. 5, 2018, in International Application No. PCT/US18/13337.

* cited by examiner

SUSPENSION TETHER FOR MEDICAL TUBING AND ATTACHMENT DEVICE FOR SAME

CROSS-REFERENCE TO RELATED APPLICATIONS

The present application claims the benefit of and priority to U.S. Provisional Patent Application No. 62/445,125, filed on Jan. 11, 2017, which is expressly incorporated herein in its entirety by reference thereto.

FIELD OF THE INVENTION

The present invention relates to a suspension tether for medical tubing and to an attachment device for such a suspension tether.

For example, a breakaway suspension tether, for attachment between an IV tree and medical, e.g., IV, tubing connected to a patient, may suspend the medical tubing off the ground, for sanitary and other reasons. Tangling of the tubing may be avoided. Inadvertent dislodgement of catheters from ambulatory patients or tipping of the IV tree may also be avoided, thereby increasing patient mobility during intravenous therapy to the full extent of the medical tubing.

An attachment device may be provided to attach to medical tubing. The attachment device may be provided separate from the medical tubing, so that attending medical personnel may select an appropriate point of attachment along the length of the tubing; alternatively, the attachment device may be provided, e.g., pre-installed or molded, at a predetermined position, e.g., approximately half-way, along the length of the IV tubing.

BACKGROUND INFORMATION

Intravenous (IV) therapy involves the administration of a therapeutic solution directly into a patient's vein or artery and is commonly used to maintain or restore fluid volume and electrolyte balance, infuse medications, transfuse blood or blood components, or to administer caloric solutions that provide nourishment to patients who cannot eat or drink due to illness or impending surgical procedures. IV therapy may be administered for time periods ranging from a few hours during a discrete procedure, to more long term situations lasting for days, weeks, or more. Short term delivery methods may range from a simple syringe push, to the ubiquitous drip bag, or to a more modern lobe pump.

It is critical with all catheters that, once inserted, they stay inserted and in place, and this is especially true of PICC lines. Should a PICC line be inadvertently dislodged, it can cause serious harm to the patient, increase the risk of infection, and, at a minimum, require a redundant surgical procedure for reinsertion.

Nevertheless, patients undergoing long-term IV therapy typically need, and want, mobility, particularly as their condition improves and are commonly seen in hospitals or at home to be walking around with their IV solution bag hanging from a rolling IV tree stand. The bag is connected to their catheter by a drip set or tube extension which is typically 72 inches to 100 inches in length and may be routed through a stand mounted battery operated pump. As patients become more mobile, they tend to move toward and away from the IV tree stand. Moving toward the IV tree stand slackens the IV tube(s), which increases the risk of tangling or unsanitary dragging along the floor, whereas moving away from the IV tree stand increases the risk that the IV tube(s) will dislodge their catheter, as that tension will tangle or kink the IV tubing preventing proper solution delivery and potentially topple the rolling tree stand, disrupting therapy, harming the patient, and damaging expensive equipment in the process.

More importantly, there is a need for patients undergoing IV therapy to keep the rolling IV tree stand at their side, as they walk, rolling the IV tree stand with them as they walk from location to location. Thus, rather than walk away from the rolling IV tree stand, even with the perceived freedom of a lengthy IV tube, the patient tends to maintain the rolling IV tree stand in close proximity. With a lengthy, or even average-length, IV tube, the IV tube will slacken, will be at risk for entanglement with the IV tree stand, its wheels, the legs or feet of the patient, other hospital equipment, etc., and will be at risk for exposure to unsanitary conditions by being dragged along the floor.

SUMMARY

Example embodiments of the present invention provide a suspension tether that allows the patient a greater freedom of movement approaching the full length or the available IV tubing, keeps the IV tubes organized, untangled and elevated to avoid snags and unsanitary conditions, and which self-detaches at a predetermined tension to provide a tactile warning when movement of the IV tube is excessive, still allowing a short reserve length of tubing beyond the threshold.

According to an example embodiment of the present invention, a breakaway elastic suspension tether is provided that keeps slack IV tubes suspended and sanitary, yet provides freedom of movement approaching the full length or the available IV tubing, thereby increasing patient mobility. The elastic suspension tether organizes the intravenous medical tubing extending between a patient and an IV stand, which supports an IV solution source such as a drip bag and lobe pump. Thus, when the patient moves toward the IV tree, the tether keeps the IV tubes suspended, sanitary, and avoids tangling about wheelchair or table wheels, chair legs, etc. The suspension tether also facilitates patient mobility as they move away from the IV tree itself, to a distance near the full length of the IV tubing, with lessened risk of pulling the tubing tight by their motion and disengaging their line or damaging the equipment.

When the patient rolls a rolling IV tree stand along his or her side while walking or otherwise moving from location to location, the tether also suspends the IV tube off the floor, tends to keep the IV tube sanitary, and avoids tangling the IV tube about the feet or legs of the patient, the tree stand or its wheels, other hospital equipment, etc. Thus, the tether addresses the situation when the patient is most vulnerable, i.e., while the patient is walking with a rolling IV tree stand at his or her side.

The suspension tether includes a linear elastic band having a grommet or other affixation hardware at one end for engaging a hook of the IV stand, and a failsafe (double) breakaway mechanism, which is attached directly to the IV tube(s) proximate their midpoint to the patient. The breakaway mechanism includes a release clip releasably attached to the IV tube(s) proximate the tube midpoint to the patient, and attached via the elastic suspension tether to a breakaway connector proximate the IV tree stand. The release clip may include a plurality of channels for seating and releasably clamping one or more lengths of medical IV tubing. A clamshell clip with pre-biased torsion spring may be provided in order to lessen the chance of kinking or compressing the tubing and thereby restricting fluid flow through the tube to the patient. The release clip may be engaged at any location along the length of the IV tube, e.g., may be engaged to the IV tube proximate the midpoint of the IV tube length, such that the length of the suspension tether is slightly longer than the half-length of the IV tubing between the point of engagement with the clip and the IV stand hook from which the solution container and/or lobe pump hangs. The extra, slack length of tubing is held as a reserve. This arrangement provides that the suspension tether is pulled tight by patient movement before the tubing is pulled tight, to provide tactile feedback to the patient, a reminder to the patient, and urging the rolling IV stand closer toward the patient. When a first threshold tension is reached, the breakaway connector releases before the IV tree is toppled, and the reserve length of tubing is quickly deployed to relieve the over-tension. This also provides tactile and/or audible feedback to the patient to avoid further overextension. Should the breakaway connector fail, the release clip disengages from the IV tubing at a second failsafe tension to prevent dislodgement of the catheter(s) and avoid serious harm to the patient.

An additional failsafe mechanism may be provided at the IV tree, e.g., by providing a breakaway mechanism located at the end of the tether most distal to the patient. For such reasons as patient safety—which is among the most important concerns—this location for a failsafe mechanism is considered beneficial, since it is most distant from the patient and least likely to be accessed or tampered with by the patient or other non-medical personnel.

While a breakaway clip may provide certain benefits, it is possible to provide an attachment device connected, or connectable to, medical tubing and connectable via a tether to an IV tree stand. The attachment device may be pre-assembled with the IV tubing, located at a predetermined position, e.g., half-way, along the length of the IV tubing. Alternatively, the attachment device may be provided separate from the IV tubing and subsequently attached to the IV tubing by medical personnel.

According to an example embodiment of the present invention, a system includes: an IV stand; at least one IV bag provided on the IV stand and containing fluid content; at least one IV tube having a proximal end fluidicly connected to a respective IV bag and a distal end adapted to deliver the fluid content contained in the IV bag to a patient via the IV tube; and an elastic suspension tether having a proximal end connected to the IV stand and a distal end connected to the IV tube between the proximal end of the IV tube and the distal end of the IV tube.

According to an example embodiment of the present invention, a device, which is connectable between an IV stand and at least one IV tube adapted to deliver fluid content contained in an IV bag provided on the IV stand and a patient, a proximal end of the IV tube connected to the IV bag, a distal end of the IV tube connectable to the patient, includes: an elastic suspension tether having a proximal end adapted to connected to the IV stand and a distal end adapted to connected to the IV tube between the proximal end of the IV tube and the distal end of the IV tube.

According to an example embodiment of the present invention, an IV fluid delivery system includes: at least one IV tube, a proximal end of the IV tube connectable to an IV bag provided on an IV stand, a distal end of the IV tube connectable to a patient, the IV tube adapted to deliver fluid content contained in the IV bag to the patient; and an elastic suspension tether having a proximal end adapted to connected to the IV stand and a distal end adapted to connected to the IV tube between the proximal end of the IV tube and the distal end of the IV tube.

A length of the elastic suspension tether may be less than a height of the IV stand.

A length of the elastic suspension tether may be approximately half a length of the IV tube.

The distal end of the elastic suspension tether may be connected to the IV tube substantially half way between the distal end of the IV tube and the proximal end of the IV tube.

The elastic suspension tether may be adapted to disconnect from the IV tube at a predetermined force.

A clip connector may be provided at the distal end of the elastic suspension tether adapted to releasably connect the elastic suspension tether to the IV tube.

The clip connector may be adapted to release the IV tube in response to a predetermined force.

The clip connector may include at least one channel adapted to receive at least one IV tube.

A diameter of the channel may substantially correspond to an outer diameter of the IV tube.

At least one rib is provided within the channel and adapted to engage the IV tube.

The IV stand may be arranged as a rollable IV stand.

The elastic suspension tether is formed of a sterilizable and/or antimicrobial material.

The IV tube may include a pre-assembled attachment device connected to the distal end of the elastic suspension tether.

The pre-assembled attachment device may include a channel, the IV tube being received in the channel.

An inside diameter of the channel may be less than or equal to an outer diameter of the IV tube.

At least one rib may be provided in the channel and may engage the IV tube.

The pre-assembled attachment device may include a first body portion and a second body portion fixed to the first body portion, and the IV tube may be provided between the first body portion and the second body portion.

The pre-assembled attachment device may include an aperture adapted to engage a connector provided at the distal end of the elastic suspension tether.

Further features and aspects of example embodiments of the present invention are described in more detail below with reference to the appended Figures.

DETAILED DESCRIPTION

Figure 1:
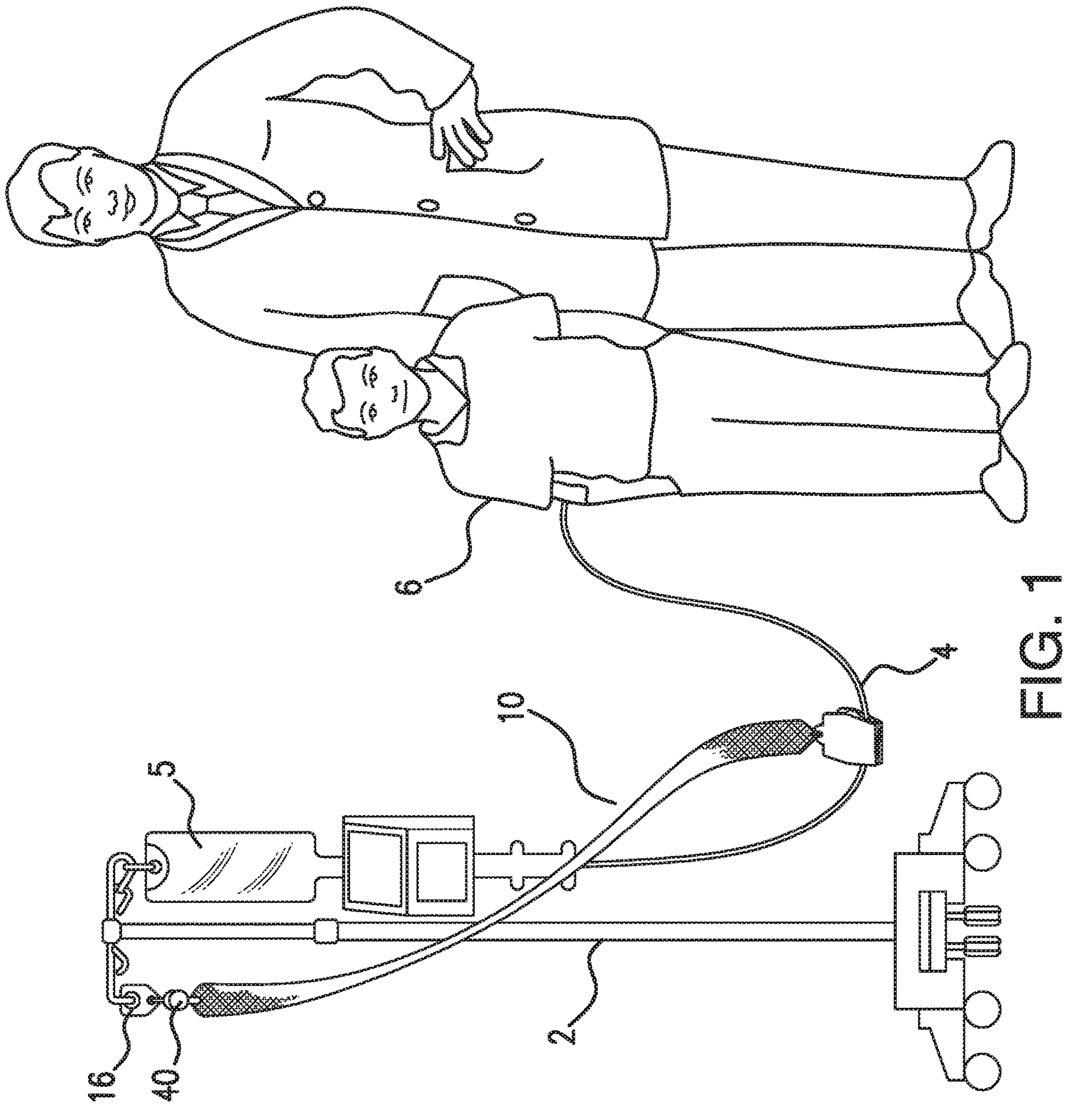
FIG. 1 is a perspective view of a suspension tether according to an example embodiment of present invention with an IV stand and patient.
Figure 2:
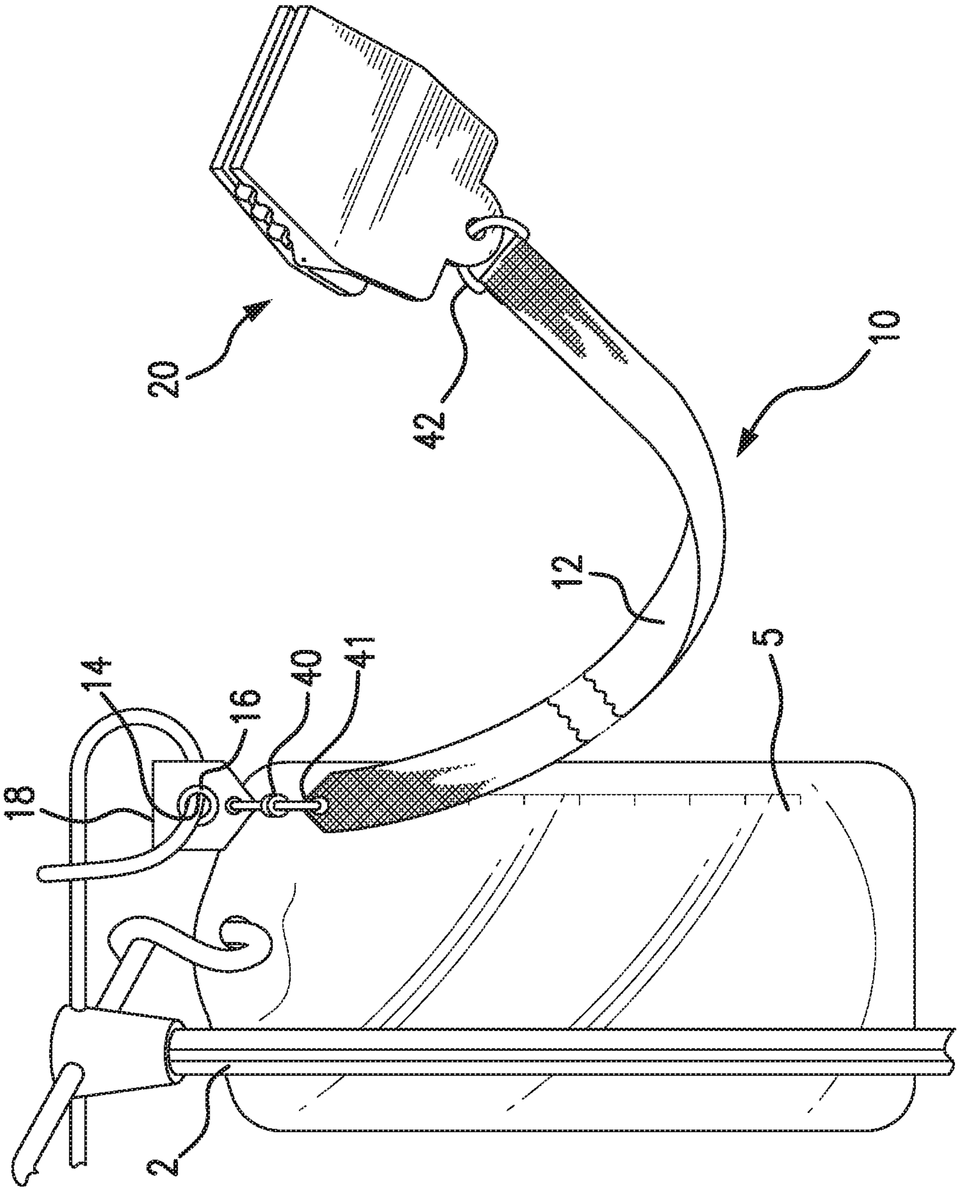
FIG. 2 is an enlarged view of the suspension tether.

FIGS. 1 and 2 illustrates a suspension tether 10 that is engaged at one end to a rolling IV tree stand 2 and at the other end to one or more IV tubes 4. The IV tube(s) 4 is/are connected at one end to an IV bag 5 and at the other end to a patient 6. The suspension tether 10 keeps the IV tube(s) 4 ordered and off the ground surface without diminishing the ability of the patient to move and generally go about his or her daily functions. Tube 4 may be any flexible medical tubing is typically a plastic or polymer tube having an outside diameter of from, e.g., 0.1 to 0.5 inches (2.5 mm to 13 mm), and a predetermined length of, e.g., 8 to 10 feet. The suspension tether 10 has an elongate body portion 12 that may be provided in the form of a flat, elasticized strap, although round elasticized cord or similar linear members may be provided. The body portion 12 may be constructed of one or more strands of an elastic material such as rubber, bound together by a fabric covering formed of nylon or cotton, and having a width of, e.g., approximately ⅜-to ½-inch. The body portion 12 may be formed of an elongated spring, e.g., covered by a sheath. The body portion 12 may be made of high-visibility material, e.g., it may be brightly or darkly colored to contrast with the typically white or light-colored walls and floors found in clinical settings.

The length of the body portion 10 may be adjustable, e.g., via a buckle, so as to be properly usable with IV stands of varying heights and IV tubing sets of various standard lengths. The desired length of the body portion 12 of the suspension tether 10 during use is slightly more than half the length of the IV tubes to which is attached, and less than the height of the IV stand with which it is used to avoid contact of the IV tube with the floor or ground in an entirely slack condition. For example, given a typical seven foot IV tree stand and eight foot IV tubes, the body portion 12 is preferably approximately 4.5' long. It should be appreciated that the length of the body portion 12 may depend on, e.g., its elasticity, elastic elongation, etc.

The body portion 12 may have a 15 to 20% stretch and recovery characteristic. As illustrated in FIG. 2, one end of the body portion 12 is engaged to the IV stand. Two to four hooks are typically provided at the top of a standard IV stand from which to hang a drip bag or other fluid container. A connector 18 is provided at the end 41 of the body portion 12 of the suspension tether 10 and connected to the end 41 of the body portion 12 by a turnbuckle or swivel connector 40. A hole 14 is provided through the connector 18 for engagement with a hook of the IV stand. The hole 14 may be reinforced with a metal or plastic grommet 16. Alternately, the periphery of the hole 14 may be bound by reinforcing stitching. The hole 14 is sized to receive the hook of the IV stand and to freely hang from the hook but yet not be easily dislodged from the hook unintentionally. A failsafe mechanism may be provided at or near the connection between the IV stand and the body portion 12. For example, the body portion 12 may be tearable or frangible proximal to the IV stand and distal to the patient, a breakaway grommet may be provided, etc.

Figure 3A:
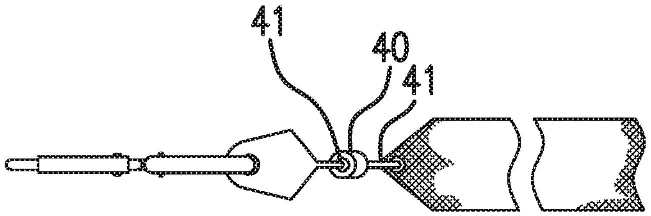
FIGS. 3A to 3F illustrate connectors for a suspension tether.
Figure 3B:
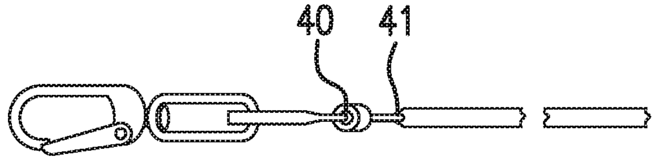
Figure 3C:
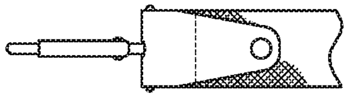
Figure 3D:
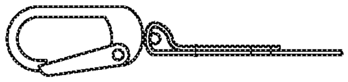

As illustrated in FIGS. 3A to 3D, a circular ring, D-ring, or clip may be proximally affixed to an end of the tether 10 for engaging a hook of the IV stand 2. The ring or clip may be made of chrome plated steel, stainless steel, brass, etc., and may be engaged to the strap by folding the strap back onto itself through the ring and stitching the end of the strap to the body portion to create a loop in which the ring is captured, as illustrated in FIGS. 3C and 3D. The clip may be arranged as a snap clip, a swivel clip, a quick-release clip, etc., and the clip may provide additional failsafe benefits by being adapted to disengage or release at a predetermined tensile force. As one example, the clip may be formed of plastic and may be designed to yield or break at a predetermined tensile force. Alternatively, the clip may be designed to open at a predetermined tensile force. Alternatively still, the clip may include two interconnected pieces that disengage when exposed to a predetermined tensile force.

The opposing end of the body portion 12 is provided with a tubing release clip 20 for receiving and grasping one or more medical IV tubes extending from one or more fluid containers engaged to the hooks of the IV stand 2. The release clip 20 includes first and second clamshell portions 22, 24, respectively. The clamshell portions 22, 24 are pivotably joined by a hinge 26 defining a lever portion 27 and a jaw portion 29 of each clamshell portion 22, 24. A pre-biased torsion spring mechanism is provided at the hinge to engage the clamshell portions 22, 24 and bias the jaw portions into a closed position in which they are in contact with one another. The torsion spring constant may be carefully selected so as to securely retain medical tubing of various diameters without crimping or reducing the cross-section of the internal lumen thereof. The jaw portions 29 remain in contact with one another under the influence of the biasing spring until sufficient pressure is applied to the lever portions to overcome the spring's biasing effect and open the jaws. This allows insertion of one or more IV tubes within the clip 20, and additionally provides a release feature.

As illustrated in FIGS. 4A to 4D, the inner surfaces of the jaw portions 29 of the clamshell portions 22, 24 include one or more longitudinal channels 30, which are adapted to receive a respective IV tube 4. Channels 30 may be formed with their longitudinal axes parallel to the axis of rotation of the hinge 26 and may be semicircular or semi-elliptical in cross-section. The channels 30 are aligned with channels on the opposing jaw portion 29 of the clamshell release clip 20 so as to form an enclosed channel within the clip 20 to receive the IV tube 4. The diameter of the channels 30 and thus of the enclosed channel may be approximately equal to the outside diameter of the intended IV tubing so as not to reduce the lumen cross section of the tube 4 and thereby impede fluid flow through the tube and to the patient when the jaws of the release clip 20 are closed. Proper selection of the spring constant of the torsion spring can accommodate oversized tubing without constricting flow through the lumen. The closed jaws apply enough pressure to the outside surface of the tubing so as to prevent the tubing from sliding through the jaws during use, and yet when a threshold tension is reached, the release clip 20 will release the IV tubes to avoid inadvertent dislodgement of catheters from the patient. For example, the spring constant is selected to release the IV tubes from clip 20 at a pre-determined tension slightly more than the tension needed for release of the breakaway connector 40 described below (the second breakaway tension), and this second breakaway tension may be quantitatively determined.

As illustrated in FIGS. 4A to 4D, one or more, e.g., one, two, or three, channels 30 may be provided, depending upon, for example, an anticipated number of IV tubes 4. If multiple channels 30 are provided, they may have the same diameters, or they may have different diameters to accommodate different sizes of IV tubes 4.

At least one lever portion 27 of the release clip 20 is provided with an aperture 32 or other arrangement for engaging the suspension tether 10. A length of round cord or chain 41 is engaged at one end to the aperture 32 and at the opposing end to the suspension tether 10.

At the other end of the body portion 12 just prior to its connection to IV stand 2 and in advance of grommet 16, a redundant breakaway mechanism may be provided, e.g., in the form of a breakaway connector 40. Breakaway connector 40 may be a barrel type breakaway connector secured to the body portion 12 and connector 18 by two lengths of cord 41. A cylindrical plug member is secured to the end of one cord 41, and a tubular receptacle member is secured to an end the other cord 41, the cords 41 being secured to the available ends of the strap of the body portion 12. The positioning of the breakaway connector 40 may be chosen to be as far from the reach of the patient as possible, e.g., to prevent children from playing with it. The tubular member has an inside diameter approximately equal to but slightly larger than the outside diameter of the cylindrical member such that the cylindrical member can be inserted into the tubular member and retained there by friction until sufficient force is applied via the cord 41 to pull the cylindrical member free. Rather than a cylindrical member, a spherical member may be provided. The cylindrical member may tapered, in which case a cooperative taper is provided within the tubular member. The breakaway connector 40 may be formed from a self-lubricating polymer such as nylon, polypropylene, PTFE, etc., although other materials having suitable friction coefficients may be utilized to achieve the desired pullout force.

As an alternative to the friction-type breakaway connector, a magnetic breakaway connector may be provided in which a magnetic element is affixed to an end of the cord 41 and a ferrous element or cooperatively aligned magnetic element is affixed to strap member 12, the attractive magnetic force joining the release clip 20 to the body portion 12 until an applied force overcomes the force of the magnetic attraction to separate the elements.

Regardless of the manner of construction, the breakaway connector 40 is adapted to release at a pre-determined tension, e.g., more than the tension needed for release of the release clip 20 but less than the tension need to tip the IV tree stand. This first breakaway tension may be quantitatively determined. The cylindrical member of the breakaway connector 40 may be engaged to the body portion 12 of the suspension tether 10 again by a short length of cord 41, and then to the IV stand 2 with grommet 16 or D-ring 42 or similar hardware element. If a D-ring is used it may be engaged to the body portion 12 by looping the strap of the body portion through the D-ring and back on itself through a slide thereby securing the D-ring 42 and providing length adjustability. The strap of the body portion 12 may be simply looped back on itself and stitched together where adjustability is not required.

Figure 3E:
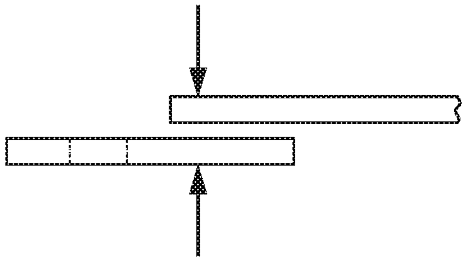
Figure 3F:
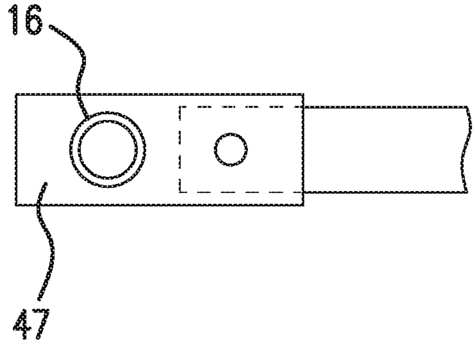
Figure 4A:
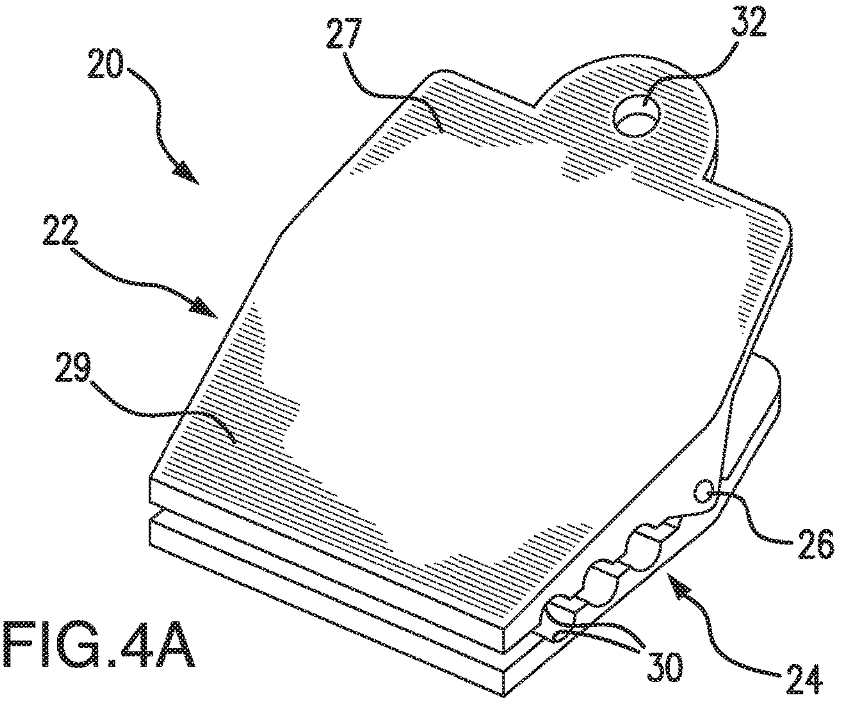
FIGS. 4A to 4D illustrate a clip portion for a suspension tether.
Figure 4B:
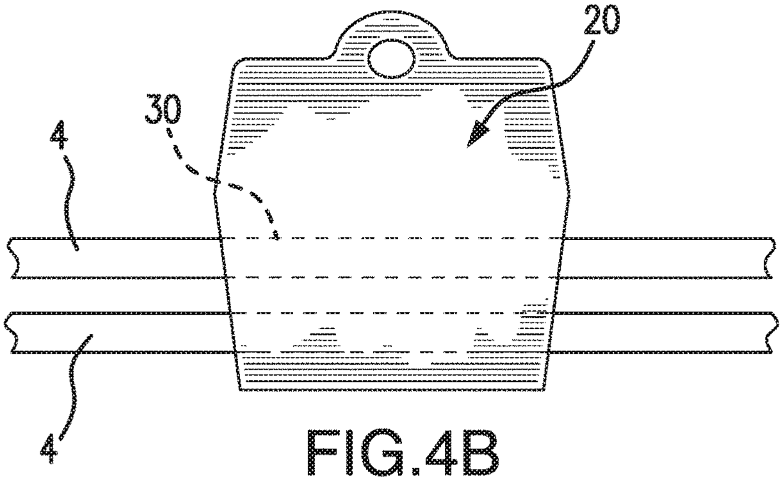
Figure 4C:
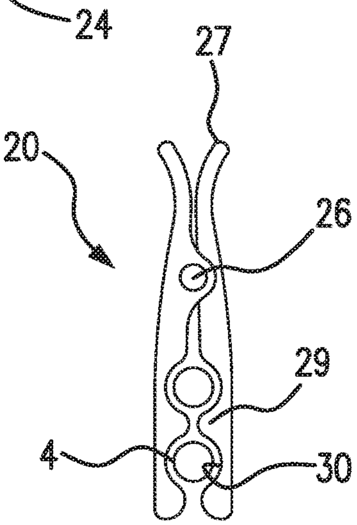
Figure 4D:
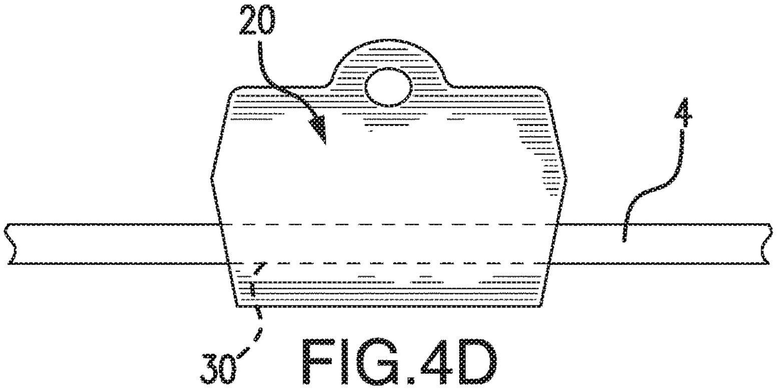

As an alternative to the breakaway connector 40, as shown in FIGS. 3E and 3F, the grommet 16 may be provided in a tearable or frangible extension 47, extension 47 being attached to the flat body portion 12 to provide the same redundant breakaway feature. The extension 47 may be formed of, e.g., paper, thin plastic, etc., adapted to tear at a predetermined tension. Overlapping portions of extension 47 and body portion 12 may be connected to each other by a hook-and-loop, e.g., Velcro, connection, a magnetic connection, low-shear adhesive connection, etc., to provide for separation at a predetermined tensile force to thereby provide a failsafe, breakaway feature.

In use, the suspension tether is suspended from a hook of an IV stand 2 by slipping the grommet 16 over the hook where it hangs freely. One or more IV solution containers, typically a bag 5 but alternately a bottle or other container, are suspended from an adjacent hook and fed through a pump, and an IV tube or tubes 4 are arranged as desired between the patient's intravenous line and the solution(s) by the attending medical professional. A lobe pump, hemodialysis unit, other active flow-control device, etc., may be provided in conjunction with one or more the IV tubes 4. Once configured as desired, the jaws 29 of the clip 20 are separated by depressing the lever portions 27, and the IV tube or tubes 4 are each aligned with one of the channels 30. The lever portions 27 are then released, and the jaws 29 close under force of the biasing spring so as to capture the IV tube(s) 4 within the release clip 20. The release clip 20 may be positioned along the tubes 4 slightly beyond the midpoint of the tube length, just beyond midway to the patient, e.g., 4.5 feet along the IV tubes 4. More specifically, the clip may be positioned such that the distance along the medical tubing from the clip to the last point of fixed engagement with the IV stand should be just greater than the length of the suspension tether 10 as measured between the grommet 16 and the channels 30 engaged to the tubing. Where a drip bag or similarly suspended container is used, the last point of fixed engagement with the IV stand is the hook on which the bag hangs and the length of tubing is considered to include the solution container and related fittings which hang freely. Where a pump or similar device is used the last point of fixed engagement with the IV stand is the point at which the tube leaves the pump or other device. The slack portion of the IV tube(s) 4 which represents the amount by which the tube length exceeds the suspension tether length is held close to the IV stand 2 in reserve.

The patient is then permitted to move about the room in order to go about his or her daily business and is able to move away from the IV stand 2 a distance that is nearly equal to the entire length of the IV tube 4. As the patient nears the maximum length of travel, but before the IV tubing is pulled tight, the suspension tether 10 is tensioned and elastic body begins to stretch, gently urging a (rolling) IV stand 2 closer to the patient and providing the patient with a soft reminder that he or she is attached to the IV line. In certain instances, such as a quick movement of the arm in which a line is peripherally inserted, the movement by the patient will be too abrupt for the suspension tether 10 to compensate by moving the stand and a gentle reminder will be too late. In such an instance, the first threshold tension in the suspension tether 10 is reached and the breakaway connector 40 activates to release the clip 20 still engaged to the tubing and thereby releasing portion of the IV tubing held in reserve. This quick increase in available tubing length reduces tension and prevents the patient from pulling the tubing too hard and upsetting the catheter or the equipment inadvertently. This also serves again to remind the patient of the IV tube's presence and to reset the suspension tether for future warnings. In addition to the early warning system the channels of the clip 20 retain the tubes relative to one another (where more than one tube is in place) and prevent entanglement.

If for any reason the breakaway connector 40 fails to operate, the clip 20 itself will release the IV tubes, thereby ensuring failsafe operation.

On the other hand, if the patient is in proximity to the IV stand 2, the tether 10 keeps the IV tubes suspended off the ground, sanitary, and tangle-free. Thus, when the patient becomes most mobile, he or she also becomes most vulnerable to entanglement of the IV tube with his or her feet or legs, with the IV tree stand or its wheels, with other hospital equipment, etc. This is because as a patient becomes more mobile, he or she is most likely to walk or otherwise travel from location to location while pulling or rolling the IV tree stand at his or her side. Under these circumstances, the IV tube is most slack and most likely to become entangled with the patient or some other object.

As an alternative to the clamp 30, the IV tube 4 may be integrally molded with a flange defined by an eyelet, and the clamp may be replaced with additional breakaway connectors 40 strung directly and tied to the eyelet of the flange of the IV tube 4.

Figure 5A:
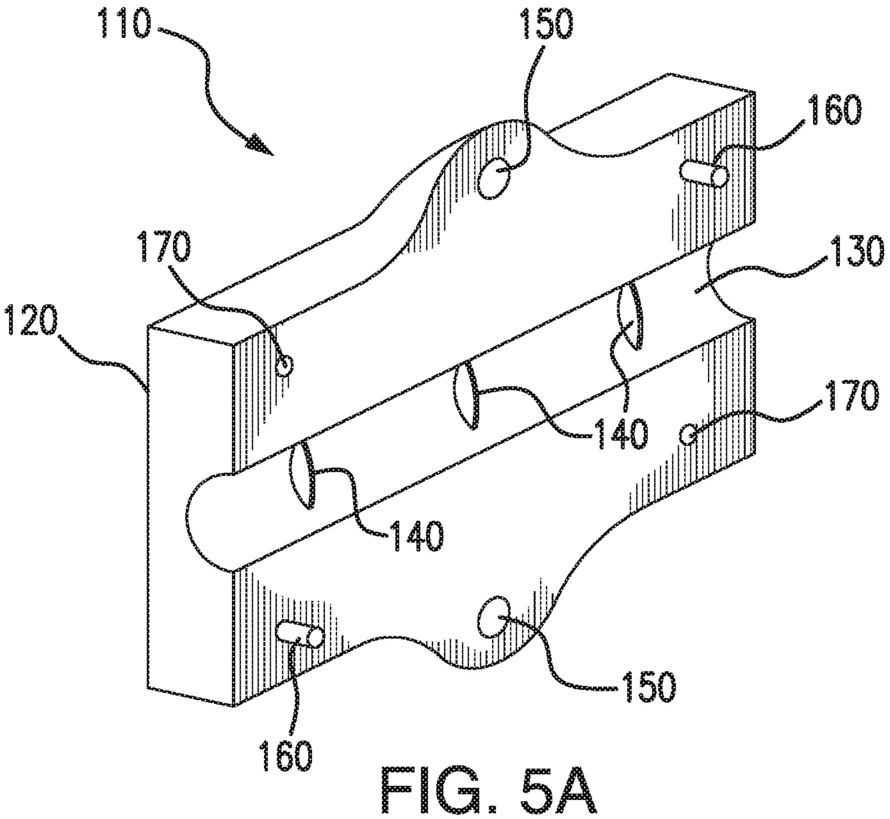
FIGS. 5A to 5C illustrate an attachment device for a suspension tether.
Figure 5B:
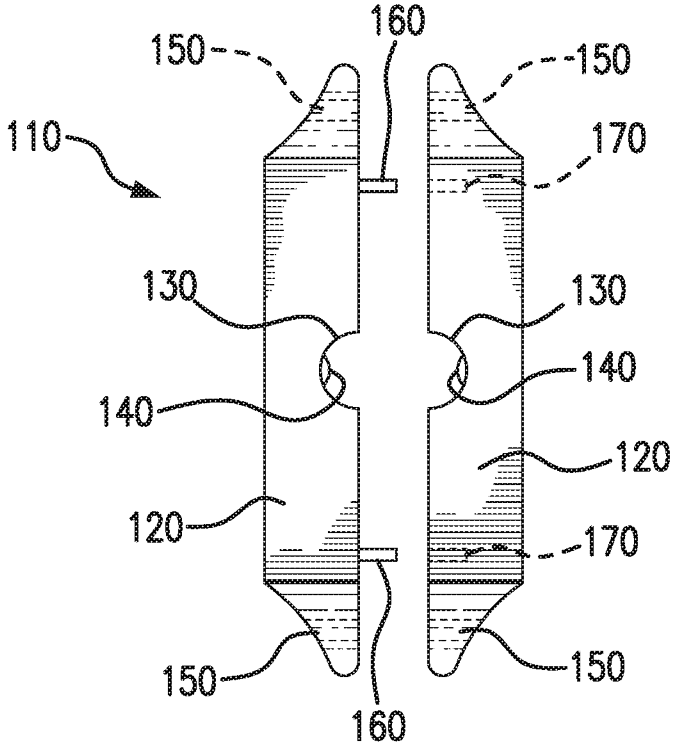
Figure 5C:
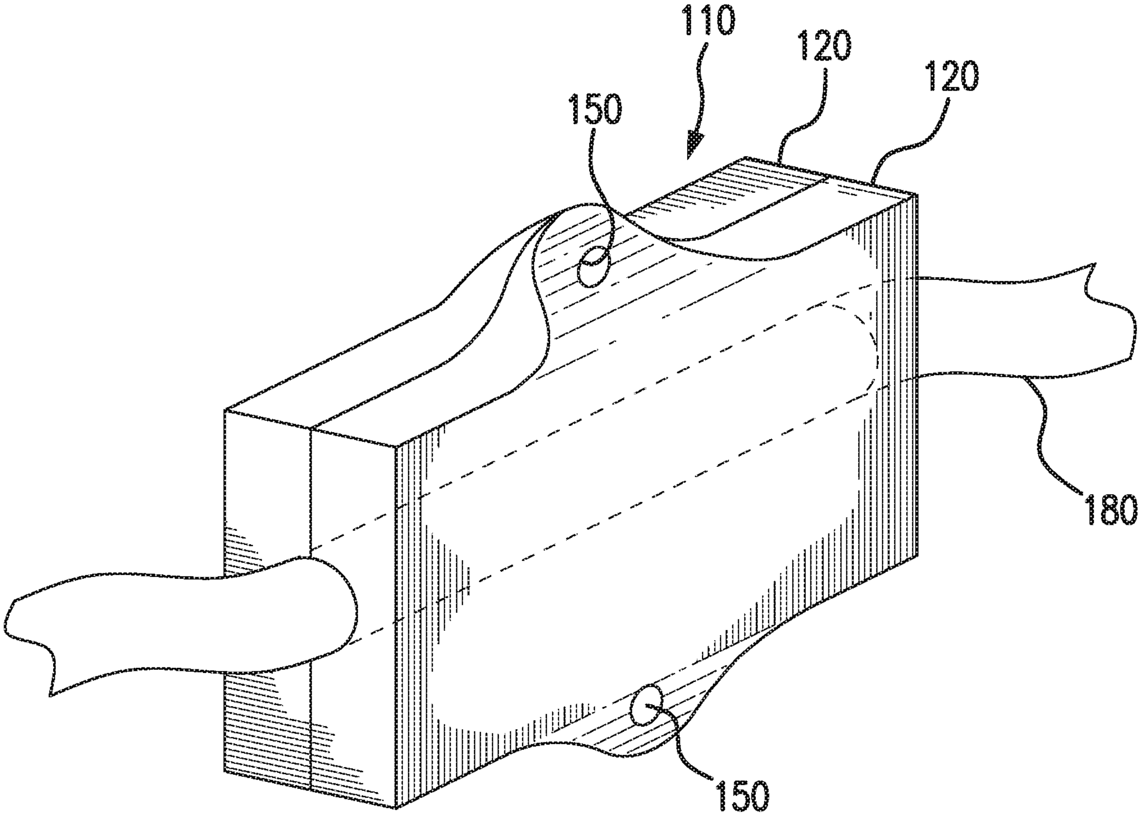

For example, as illustrated in FIGS. 5A to 5C, an attachment mechanism 110 includes two identical, and self-complimentary, body halves 120. One, or more, channels 130 are formed along the inside surface of each body halve 120 for accommodating IV tube 180; the diameter of the channel 130 may substantially correspond to the outer diameter of the IV tube 180 or may be slightly undersized to provide friction against the IV tube 180 to prevent the attachment mechanism 110 from moving along the IV tube 180 once installed thereon. To further provide for friction and avoid movement along the IV tube 180, the channel 130 may include one or more ribs 140 or other protrusions that protrude into the channel 130 and that engage the IV tube 180.

An aperture 150 is provided on one or both sides of each body halve 120 and is adapted to accommodate a clip or connector provided at the end of the suspension tether 20. One or more male fasteners 160 are provided on each body halve 120 and are located to correspond to a mating, e.g., blind, hole 170 of the other body halve 120, so that, upon assembly of the two body halves 120, the channels 130 align. A barb or other enlarged portion may be provided on the end of fastener 160 for snap-fitting, form-fitting, or frictional engagement of the two body halves 120 upon assembly.

The attachment mechanism 110 may be provided in an unassembled state, allowing for medical personnel to field-install the attachment mechanism 110 to the IV tube 180, at any desired location along the length of the IV tube 180. In this case, the attachment mechanism may be assembled by positioning the body halves 120 at the desired position along the length of the IV tube 180, with the IV tube 180 positioned within the channels 130 and the fasteners 160 and holes 170 aligned, and then pressing the two body halves 120 together. The engaged fasteners 160 and holes 170 secure the body halves 120 together and against disassembly. The tether 10 may then be connected to the attachment mechanism 110 via the aperture 150.

The attachment mechanism 110 may also be provided in the unassembled state without a length of IV tube 180, or may be provided in the unassembled state with a length of IV tube 180 as a kit.

The attachment mechanism 110 may be provided assembled with a length of IV tube 180. In this case, the two body halves 120 may be permanently connected to each other, and to the IV tube 180, by, e.g., friction-welding, ultrasonically-welding, solvent-welding, or mechanically coupling the body halves 120 together. The attachment mechanism 110 may, for example, be located midway along the length of the IV tube 180.

The components of the apparatus described herein may be formed of sterilized, sterilizable, and/or antimicrobial materials.

It should be apparent that the above-described device functions in a failsafe manner to avoid inadvertent dislodgement of catheters from ambulatory patients or tipping of the IV tree, thereby increasing patient mobility during intravenous therapy to the full extent of the medical tubing.

What is claimed is:

1. A system, comprising:

an IV stand;

an IV bag provided on the IV stand and containing fluid content;

an IV tube having a proximal end fluidicly connected to the IV bag and a distal end adapted to deliver the fluid content contained in the IV bag to a patient via the IV tube; and an elastic suspension tether formed of an elastic fabric strap, having a proximal end connected to the IV stand and a distal end connected to the IV tube between the proximal end of the IV tube and the distal end of the IV tube and adapted to provide elastic tactile feedback to the patient along a longitudinal axis of the elastic suspension tether.

2. An IV fluid delivery system, comprising:

an IV tube, a proximal end of the IV tube connectable to an IV bag provided on an IV stand, a distal end of the IV tube connectable to a patient, the IV tube adapted to deliver fluid content contained in the IV bag to the patient; and an elastic suspension tether formed of an elastic fabric strap, having a proximal end adapted to connect to the IV stand and a distal end adapted to connect to the IV tube between the proximal end of the IV tube and the distal end of the IV tube and adapted to provide elastic tactile feedback to the patient along a longitudinal axis of the elastic suspension tether;

wherein the IV tube includes a pre-assembled attachment device located at a predetermined fixed location along a length of the IV tube, the distal end of the elastic suspension tether adapted to connect to the pre-assembled attachment device.

3. An IV fluid delivery system, comprising:

an IV tube, a proximal end of the IV tube connectable to an IV bag provided on an IV stand, a distal end of the IV tube connectable to a patient, the IV tube adapted to deliver fluid content contained in the IV bag to the patient; and an elastic suspension tether formed of an elastic fabric strap, having a proximal end adapted to connect to the IV stand and a distal end adapted to connect to the IV tube between the proximal end of the IV tube and the distal end of the IV tube and adapted to provide elastic tactile feedback to the patient along a longitudinal axis of the elastic suspension tether;

wherein an attachment device is molded to the IV tube at a predetermined fixed location approximately half way along a length of the IV tube and adapted to connect to the distal end of the elastic suspension tether.

4. An IV fluid delivery system, comprising:

an IV tube, a proximal end of the IV tube connectable to an IV bag provided on an IV stand, a distal end of the IV tube connectable to a patient, the IV tube adapted to deliver fluid content contained in the IV bag to the patient; and an elastic suspension tether formed of an elastic fabric strap, having a proximal end adapted to connect to the IV stand and a distal end adapted to connect to the IV tube between the proximal end of the IV tube and the distal end of the IV tube and adapted to provide elastic tactile feedback to the patient along a longitudinal axis of the elastic suspension tether;

wherein an attachment device is molded to the IV tube at a predetermined fixed location along a length of the IV tube and adapted to connect to the distal end of the elastic suspension tether.

5. The system according to claim 1, wherein a length of the elastic suspension tether is less than a height of the IV stand and/or approximately half a length of the IV tube.

6. The system according to claim 1, wherein the distal end of the elastic suspension tether is connected to the IV tube substantially half way between the distal end of the IV tube and the proximal end of the IV tube.

7. The system according to claim 1, wherein the elastic suspension tether is adapted to disconnect from the IV tube at a predetermined force.

8. The system according to claim 1, wherein a clip connector is provided at the distal end of the elastic suspension tether adapted to releasably connect the elastic suspension tether to the IV tube.

9. The system according to claim 8, wherein the clip connector is adapted to release the IV tube in response to a predetermined force.

10. The system according to claim 8, wherein the clip connector includes a channel adapted to receive the IV tube.

11. The system according to claim 10, wherein a diameter of the channel substantially corresponds to an outer diameter of the IV tube.

12. The system according to claim 10, wherein a rib is provided within the channel and adapted to engage the IV tube.

13. The system according to claim 1, wherein the IV stand is arranged as a rollable IV stand.

14. The system according to claim 1, wherein the elastic suspension tether is formed of a sterilizable and/or antimicrobial material.

15. The system according to claim 1, wherein the IV tube includes a pre-assembled attachment device located at a predetermined fixed position along a length of the IV tube and connected to the distal end of the elastic suspension tether.

16. The system according to claim 15, wherein the pre-assembled attachment device includes a channel, the IV tube being received in the channel.

17. The system according to claim 16, wherein an inside diameter of the channel is less than or equal to an outer diameter of the IV tube.

18. The system according to claim 16, wherein a rib is provided in the channel and engages the IV tube.

19. The system according to claim 15, wherein the pre-assembled attachment device includes a first body portion and a second body portion fixed to the first body portion, the IV tube being provided between the first body portion and the second body portion.

20. The system according to claim 15, wherein the pre-assembled attachment device includes an aperture adapted to engage a connector provided at the distal end of the elastic suspension tether.

21. The IV fluid delivery system according to claim 2, wherein a length of the elastic suspension tether is less than a height of the IV stand and/or approximately half a length of the IV tube.

22. The IV fluid delivery system according to claim 2, wherein the fixed location is substantially half way between the distal end of the IV tube and the proximal end of the IV tube.

23. The IV fluid delivery system according to claim 2, wherein the elastic suspension tether is adapted to disconnect from the attachment device at a predetermined force.

24. The IV fluid delivery system according to claim 2, further comprising a clip connector provided at the distal end of the elastic suspension tether adapted to releasably connect the elastic suspension tether to the attachment device.

25. The IV fluid delivery system according to claim 24, wherein the clip connector is adapted to release the attachment device in response to a predetermined force.

26. The IV fluid delivery system according to claim 4, wherein the attachment device includes a channel that receives the IV tube.

27. The IV fluid delivery system according to claim 26, wherein a diameter of the channel substantially corresponds to an outer diameter of the IV tube.

28. The IV fluid delivery system according to claim 26, wherein a rib is provided within the channel and adapted to engage the IV tube.

29. The IV fluid delivery system according to claim 2, wherein the IV stand is arranged as a rollable IV stand.

30. The IV fluid delivery system according to claim 2, wherein the elastic suspension tether is formed of a sterilizable and/or antimicrobial material.

31. The IV fluid delivery system according to claim 4, wherein the attachment device includes a channel, the IV tube being received in the channel.

32. The IV fluid delivery system according to claim 31, wherein an inside diameter of the channel is less than or equal to an outer diameter of the IV tube.

33. The IV fluid delivery system according to claim 31, wherein a rib is provided in the channel and engages the IV tube.

34. The IV fluid delivery system according to claim 4, wherein the attachment device includes a first body portion and a second body portion fixed to the first body portion, the IV tube being provided between the first body portion and the second body portion.

35. The IV fluid delivery system according to claim 4, wherein the attachment device includes an aperture adapted to engage a connector provided at the distal end of the elastic suspension tether.

36. The IV fluid delivery system according to claim 4, wherein a length of the elastic suspension tether is less than a height of the IV stand and/or approximately half a length of the IV tube.

37. The IV fluid delivery system according to claim 4, wherein the predetermined fixed location is substantially half way between the distal end of the IV tube and the proximal end of the IV tube.

38. The IV fluid delivery system according to claim 4, wherein the elastic suspension tether is adapted to disconnect from the attachment device at a predetermined force.

39. The IV fluid delivery system according to claim 4, further comprising a clip connector provided at the distal end of the elastic suspension tether adapted to releasably connect the elastic suspension tether to the attachment device.

40. The IV fluid delivery system according to claim 39, wherein the clip connector is adapted to release the attachment device in response to a predetermined force.

41. The IV fluid delivery system according to claim 39, wherein the attachment device includes a channel adapted to receive the IV tube.

42. The IV fluid delivery system according to claim 41, wherein a diameter of the channel substantially corresponds to an outer diameter of the IV tube.

43. The IV fluid delivery system according to claim 41, wherein a rib is provided within the channel and adapted to engage the IV tube.

44. The IV fluid delivery system according to claim 4, wherein the IV stand is arranged as a rollable IV stand.

45. The IV fluid delivery system according to claim 4, wherein the elastic suspension tether is formed of a sterilizable and/or antimicrobial material.

46. The IV fluid delivery system according to claim 2, wherein the pre-assembled attachment device includes a channel, the IV tube being received in the channel.

47. The IV fluid delivery system according to claim 46, wherein an inside diameter of the channel is less than or equal to an outer diameter of the IV tube.

48. The IV fluid delivery system according to claim 46, wherein a rib is provided in the channel and engages the IV tube.

49. The IV fluid delivery system according to claim 2, wherein the pre-assembled attachment device includes a first body portion and a second body portion fixed to the first body portion, the IV tube being provided between the first body portion and the second body portion.

50. The IV fluid delivery system according to claim 2, wherein the attachment device includes an aperture adapted to engage a connector provided at the distal end of the elastic suspension tether.

51. The system according to claim 1, wherein an attachment device is molded to the IV tube at a predetermined fixed position approximately half way along a length of the IV tube and adapted to connect to the distal end of the elastic suspension tether.

52. The IV fluid delivery system according to claim 2, wherein the attachment device is molded to the IV tube at the predetermined fixed location along the length of the IV tube.

53. The system according to claim 1, wherein an attachment device is molded to the IV tube at a predetermined fixed position along a length of the IV tube and adapted to connect to the distal end of the elastic suspension tether.

* * * * *